US008114632B2

(12) United States Patent
Melarkode et al.

(10) Patent No.: US 8,114,632 B2
(45) Date of Patent: Feb. 14, 2012

(54) METHOD OF PRODUCING BIOLOGICALLY ACTIVE POLYPEPTIDE HAVING INSULINOTROPIC ACTIVITY

(75) Inventors: Ramakrishnan Melarkode, Bangalore (IN); Akundi Venkata Sriram, Bangalore (IN); Kedarnath Nanjund Sastry, Bangalore (IN); Lakshmi Prabha Varadarajalu, Bangalore (IN); Shrikumar Suryanarayan, Bangalore (IN)

(73) Assignee: Biocon Limited, Bangalore, Karnataka (IN)

( * ) Notice: Subject to any disclaimer, the term of this patent is extended or adjusted under 35 U.S.C. 154(b) by 344 days.

(21) Appl. No.: 12/305,460

(22) PCT Filed: Jun. 20, 2007

(86) PCT No.: PCT/IN2007/000241
§ 371 (c)(1),
(2), (4) Date: Dec. 18, 2008

(87) PCT Pub. No.: WO2007/148345
PCT Pub. Date: Dec. 27, 2007

(65) Prior Publication Data
US 2010/0167342 A1    Jul. 1, 2010

(30) Foreign Application Priority Data

Jun. 21, 2006  (IN) ............................ 1057/CHE/2006

(51) Int. Cl.
*C12N 15/09* (2006.01)
*C12N 15/74* (2006.01)
*C12P 21/06* (2006.01)
*C12P 21/04* (2006.01)

(52) U.S. Cl. ..................... 435/69.4; 435/69.1; 435/69.9; 435/71.1; 435/471

(58) Field of Classification Search .......................... None
See application file for complete search history.

(56) References Cited

U.S. PATENT DOCUMENTS 5,424,286 A * 6/1995 Eng ................................. 514/5.9
6,723,530 B1 * 4/2004 Drucker ........................ 435/69.1

FOREIGN PATENT DOCUMENTS

| CN | 1635117 A | 7/2005 |
| EP | 978565 | 10/2007 |
| WO | WO 98/35033 | 8/1998 |
| WO | WO 99/07404 | 2/1999 |

OTHER PUBLICATIONS

Boehm et al., "Disruption of the KEX1 Gene in *Pichia pastoris* Allows Expression of Full-Length Murine and Human Endostatin"; Yeast, 15, pp. 563-572, May 1999.
Goke et al., "Exendin-4 is High Potency Agonist and Truncated Exendin-(9-39)-amide an Antagonist at the Glucagon-like Peptide 1-(7-36)-amide Receptor of Insulin-secreting β-Cells*", The Journal Biological Chemistry,vol. 268, No. 26, pp. 19650-19655, Sep. 15, 1993.
Kjeldsen et al., "Secretory expression and characterization of insulin in Pichia postoris", Biotechnol. Appl. Biochem. 29, pp. 79-86, 1999.
Pohl et al., "Molecular Cloning of the Helodermin and Exendin-4 cDNAs in the Lizard", The Journal of Biological Chemistry, vol. 273, No. 16, pp. 9778-9784, 1998.
Raufman, Jean-Pierre; "Bioactive peptides from lizard venoms", Elsevier Sciences B.V., Reg. Peptides, 61; pp. 1-18, 1996.
Rendueles et al., "Identification of the Structural Gene for Dipeptidyl Aminopeptidase yscV (DAP2) of *Saccharomyces cerevisiae*", Journal of Bacteriology, vol. 169, No. 9, pp. 4041-4048, Sep. 1987.
Werten et al., "Reduced Proteolysis of Secreted Gelatin and Yps1-Mediated α-Factor Leader Processing in a *Pichia pastoris kex2* Disruptant", Applied and Environmental Microbiology, 71(5): pp. 2310-2317, May 2005.
Yi L et al., "Protein Pept Lett.", PubMed, Medline, 13(8), pp. 823-827, 2006. (abstract).
Young et al, "Glucose-Lowering and Insulin-Sensitizing Actions of Exendin-4", Diabetes 48; pp. 1026-1034, 1999.

* cited by examiner

*Primary Examiner* — Shulamith H Shafer
(74) *Attorney, Agent, or Firm* — Harness, Dickey & Pierce, PLC

(57) ABSTRACT

The present invention relates to a method of producing a biologically active polypeptide having insulinotropic activity, the method comprising steps of: (a) transforming a genetically modified host cell that has protease gene knockout, with a polynucleotide vector encoding the polypeptide; and (b) growing the transformed host cell to produce the biologically active polypeptide; and a method of producing a biologically active polypeptide having an N-terminal recognition site His-Gly with insulinotropic activity, the method comprising steps of: (a) transforming a genetically modified *Pichia pastoris* that has protease gene STE13 knockout, with a polynucleotide vector encoding the polypeptide; and (b) growing the transformed *Pichia pastoris* to produce the biologically active polypeptide.

14 Claims, 9 Drawing Sheets

US 8,114,632 B2

Figure 1:
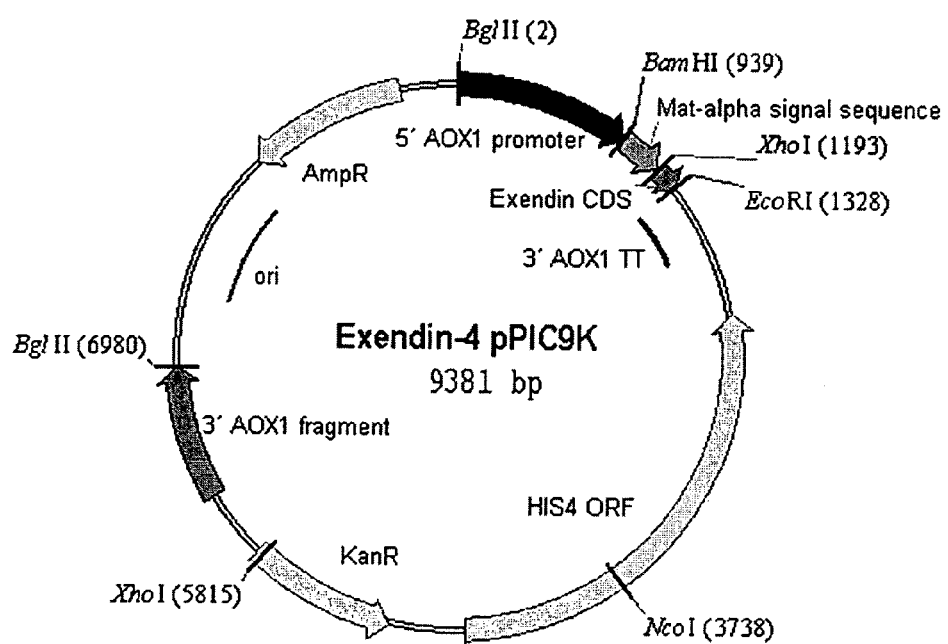

METHOD OF PRODUCING BIOLOGICALLY ACTIVE POLYPEPTIDE HAVING INSULINOTROPIC ACTIVITY

FIELD OF THE INVENTION

The present invention provides a system for producing an insulinotropic peptide (e.g., Exendin-4) by cloning and expressing the native peptide or an engineered form of the peptide in a genetically modified microorganism(s) such as yeast wherein the aminopeptidase gene is disrupted, to enable efficient expression of the full length protein or polypeptide.

BACKGROUND AND PRIOR ART OF THE INVENTION

Exendins are a family of peptides that lower blood glucose levels and have some sequence similarity (53%) to GLP-1 (Goke et al., 1993 *J. Biol. Chem.* 268; 19650-19655; incorporated herein by reference). The exendins are found in the venom of the Gila Monster (*Heloderma suspectum*; Raufman 1996 *Reg. Peptides,* 61; 1-18; incorporated herein by reference) and the Mexican beaded lizard. Exendin-4 found in the venom of the Gila Monster is of particular interest. The Exendin-4 precursor is a 87 amino acid polypeptide that includes signal and prosequences (Sequence ID No: 1). It is processed to give the amidated 39 amino acid Exendin-4 (Sequence ID No: 2). Published PCT international patent application, WO 98/35033, which is incorporated herein by reference, discloses the cDNA encoding proexendin peptide, including exendin and other novel peptides, its isolation, and antibodies which specifically recognize such peptides (Pohl et al. 1998, *J. Biol. Chem.* 273; 9778-9784; incorporated herein by reference). Exendin-4 has been shown to be a strong agonist of the GLP-1 receptor in isolated rat insulinoma cells. It also has a greater biological half-life compared to GLP-1 (Young et al 1999 *Diabetes* 48; 1026-1034; incorporated herein by reference). This may be expected since the His-Ala domain of active GLP-1 (Sequence ID No: 3) recognized by DPP-IV is not present in Exendin-4, which has the sequence His-Gly instead.

Exendin-4 given systemically lowers blood glucose levels by 40% in diabetic db/db mice (WO 99/07404; incorporated herein by reference). U.S. Pat. No. 5,424,286 by Eng, which is incorporated herein by reference, discloses that a considerable portion of the N-terminal sequence is essential in order to preserve insulinotropic activity.

The number of amino acid residues in a peptide sequence has a dramatic influence on the production costs of peptides made by solid phase synthetic chemistry. The cost of manufacturing a 50-mer peptide is at least 5 times greater than the cost of a 10-mer peptide. Solid phase peptide synthesis also requires the use of corrosive solvents such as TFS and hydrofluoric acids, a number of synthetic steps are required to produce the peptide, and subsequent purification of the peptide. Therefore, there is a need for an efficient and cost effective method for producing large quantities of biologically active Exendin-4 and other insulinotropic peptides.

Expression of a recombinant protein or polypeptide in *Pichia* or other microorganisms does not always result in successful production of full length polypeptide. Often, the heterologous recombinant polypeptide/protein are subjected to cleavage/degradation by proteases intracellularly. Given the structure of a protein and the multiplicity of proteases present in the cell, specificity of the amino acid sequence recognized by or targeted by the protease is in many cases undetermined and not published. It is therefore not always possible for a person skilled in the art to guess which protease would be responsible for cleavage/degradation of a specific recombinant polypeptide/protein. For eg., it has been reported that expression of murine or human endostatin in *Pichia* led to a product which was missing C-terminal lysine (Folkman et al, 1999 May; 15(7):563-72). When the *Pichia* homologue of KEX-1 gene of *Saccharomyces cerevisiae* was disrupted, the *Pichia* host secreted full length endostatin into the medium. In another study it was reported that disruption of KEX-2, but not YPS-1 gene, in *Pichia* allowed production of mammalian gelatin, which was being cleaved at monoargylinic sites of the protein (Werten and de Wolf, Applied and Environmental Microbiology, 2005 May; 71(5):2310-7).

The instant invention proves the prevention of in vivo proteolytic cleavage of proteins/polypeptide having the amino acids HG (His-Gly) at the N-terminus with the disruption of *Saccharomyces cerevisiae* STE13 gene homolog of *Pichia*. Very specifically the problem associated with proteolytic cleavage of Glycine-extended Exendin-4 (GlyExendin-4, Exendin-4 precursor with C-terminal glycine) has been shown to be solved by disruption of *Saccharomyces cerevisiae* STE13 gene homolog of *Pichia*.

```
GLYEXENDIN-4
                                     (Sequence ID No: 4)
HGEGTFTSDLSKQMEEEAVRLFIEWLKNGGPSSGAPPPSG
```

OBJECTS OF THE INVENTION

The principal object of the present invention is to produce a biologically active polypeptide.

Another main object of the present invention is to produce an insulinotropic peptide Exendin-4.

Yet another object of the present invention is to develop a method for producing the insulinotropic peptide.

Yet another object of the present invention is to develop a method of expressing a full length polypeptide from Pichia host cell.

Yet another object of the present invention is to develop a method of amidating the insulinotropic peptide.

STATEMENT OF THE INVENTION

The present invention relates to a method of producing a biologically active polypeptide having an N-terminal recognition site His-Gly, with insulinotropic activity, the method comprising steps of: (a) transforming a genetically modified host cell that has protease gene knockout, with a polynucleotide vector encoding the polypeptide: and (b) growing the transformed host cell to produce the biologically active polypeptide; and a method of producing a biologically active polypeptide having an N-terminal recognition site His-Gly with insulinotropic activity, the method comprising steps or: (a) transforming a genetically modified *Pichia pastoris* that has protease gene STE13 knockout with a polynucleotide vector encoding the polypeptide: and (b) growing the transformed *Pichia pastoris* to produce the biologically active polypeptide.

DETAILED DESCRIPTION OF THE INVENTION

The present invention relates to a method of producing a biologically active polypeptide having an N-terminal recognition site His-Gly with insulinotropic activity, the method comprising steps of:
 a. transforming a genetically modified host cell that has protease gene knockout, with a polynucleotide vector encoding the polypeptide: and
 a. transforming a genetically modified host cell that has protease gene knockout, with a poly nucleotide vector encoding the polypeptide: and
 b. growing the transformed host cell to produce the polypeptide: and
 c. alpha amidating the polypeptide to produce biologically active polypeptide.

In still another embodiment of the present invention, the host cell is yeast cell.

In still another embodiment of the present invention, the yeast cell is *Pichia pastoris*.

In still another embodiment of the present invention, the protease gene STE13 gene.

In still another embodiment of the present invention, the protease gene is an N-terminal dipeptidyl peptidase gene.

In still another embodiment of the present invention, the method involves growing the transformed cells under conditions which induce expression of the polypeptide.

The present invention also relates to a method of producing a biologically active polypeptide having an N-terminal recognition site His-Gly with insulinotropic activity, the method comprising steps of:
 a. transforming a genetically modified *Pichia pastoris* that has protease gene STE13 knockout, with a polynucleotide vector encoding the polypeptide: and
 b. growing the transformed *Pichia pastoris* to produce the biologically active polypeptide.

In still another embodiment of the present invention, the polypeptide is Glyexendin-4 of SEQ ID No 4.

In still another embodiment of the present invention the Glyexendin-4 has corresponding polynucleotide sequence of SEQ ID No. 5.

In still another embodiment of the present invention, the method involves contacting the glyexedin-4 polypeptide with a C-terminal alpha-amidating enzyme to yield an alpha-amidated exendin-4 polypeptide.

In still another embodiment of the present invention, the alpha-amidated exendin-4 polypeptide is HGEGTFTSDL-SKQMEEEAVRLFIEWLKNGGPSSGAPPPS-NH2 (SEQ ID NO. 2).

BRIEF DESCRIPTION OF ACCOMPANYING DRAWINGS

FIG. 1 A construct for expression of GlyExendin-4 in *Pichia pastoris*.

Figure 2:
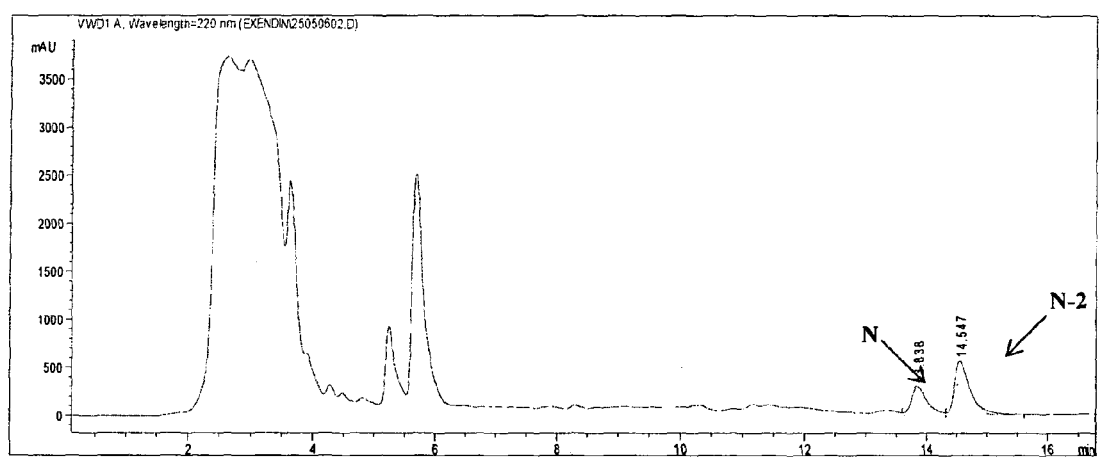

FIG. 2 HPLC chromatogram showing two peaks of Gly-Exendin-4-N and N-2 (i.e. N-terminally cleaved GlyExendin-4).

Figure 3:
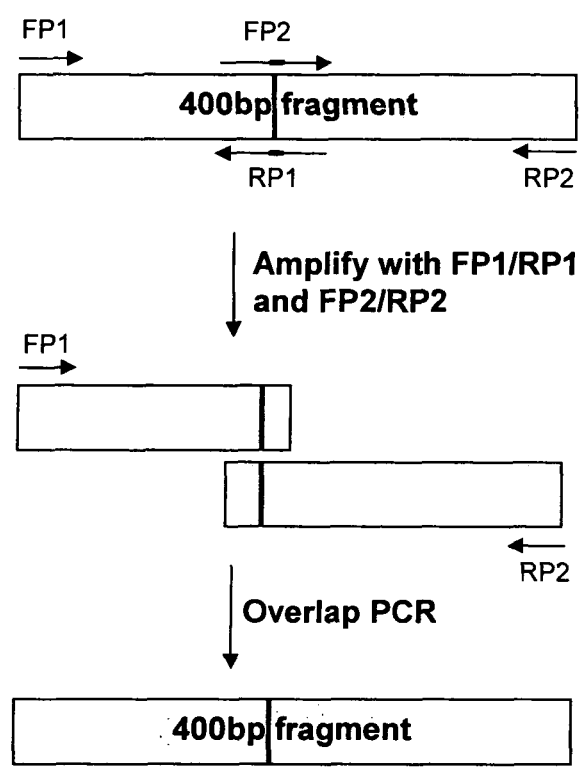
Figure 4:
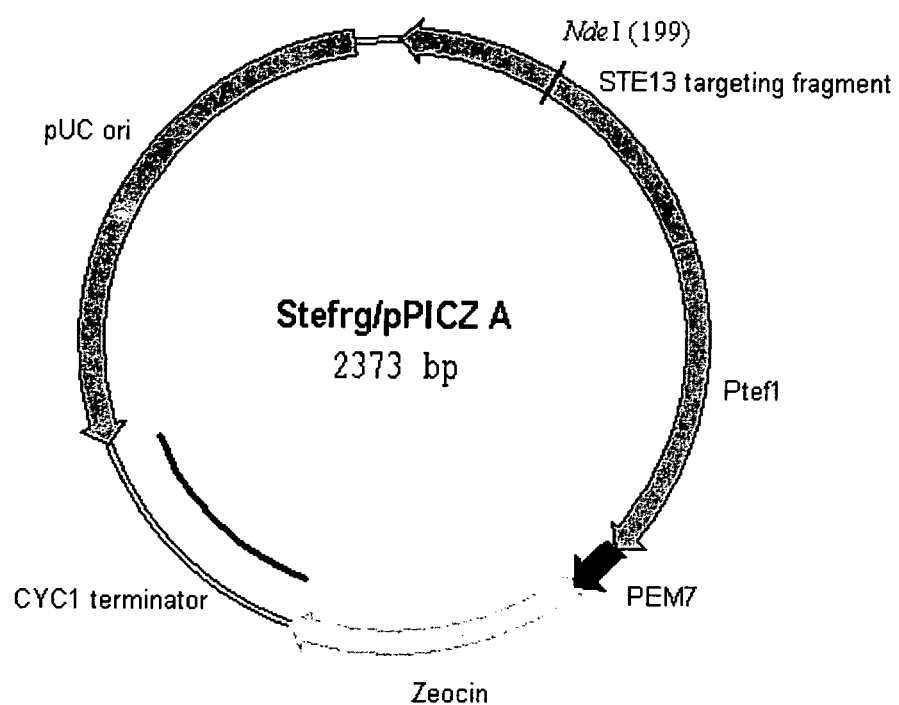
Figure 5:
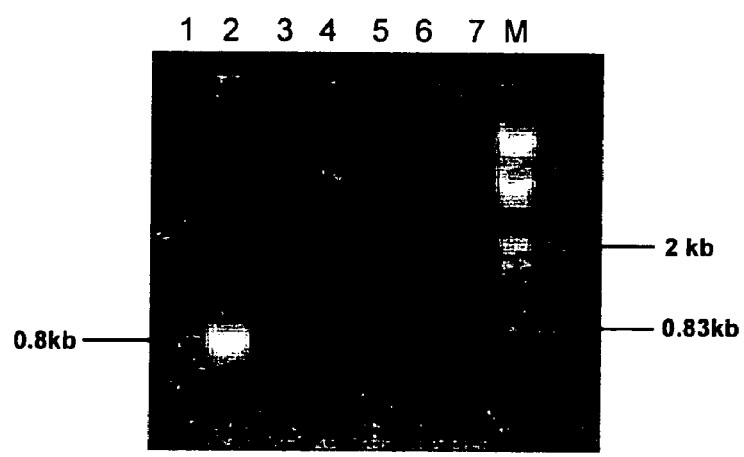

FIG. 3 Strategy for introduction of NdeI restriction site into the STE13 gene fragment amplified from *Pichia pastoris* genome by PCR FIG. 4 A construct for disruption of genomic copy of the *Pichia* homolog of *Saccharomyces cerevisiae* STE13 gene FIG. 5 PCR analysis of putative disruptants. PCR products amplified from genomic DNA of clones D2, D4, D6, D8, D10, D12 (Lanes 2-7) and GS115 (Lane 1).

Figure 6:
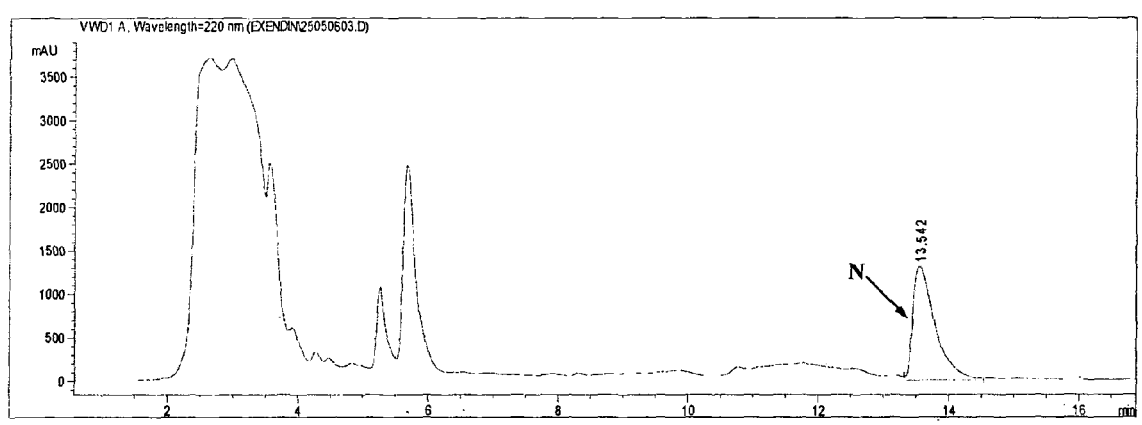

FIG. 6 HPLC chromatogram showing full length-GlyExendin-4 from STE13 gene disrupted *Pichia pastoris* host.

Figure 7:
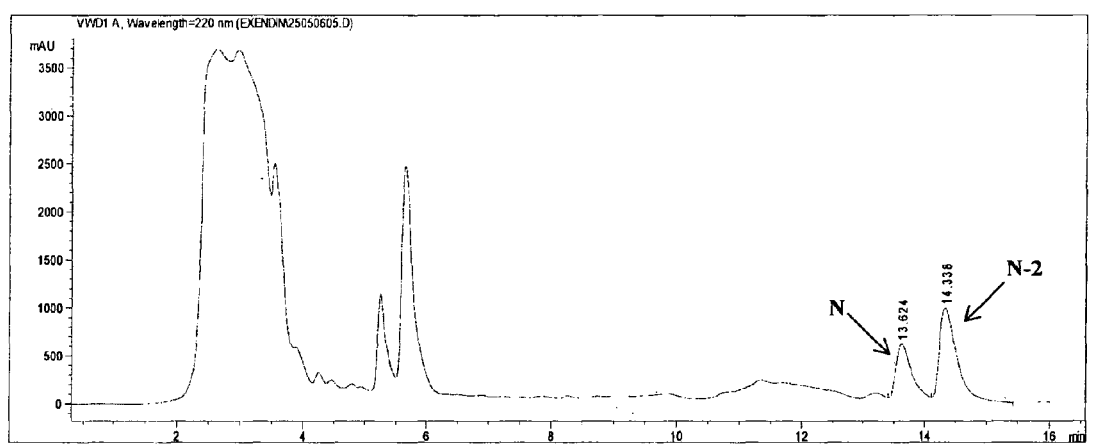
Figure 8:
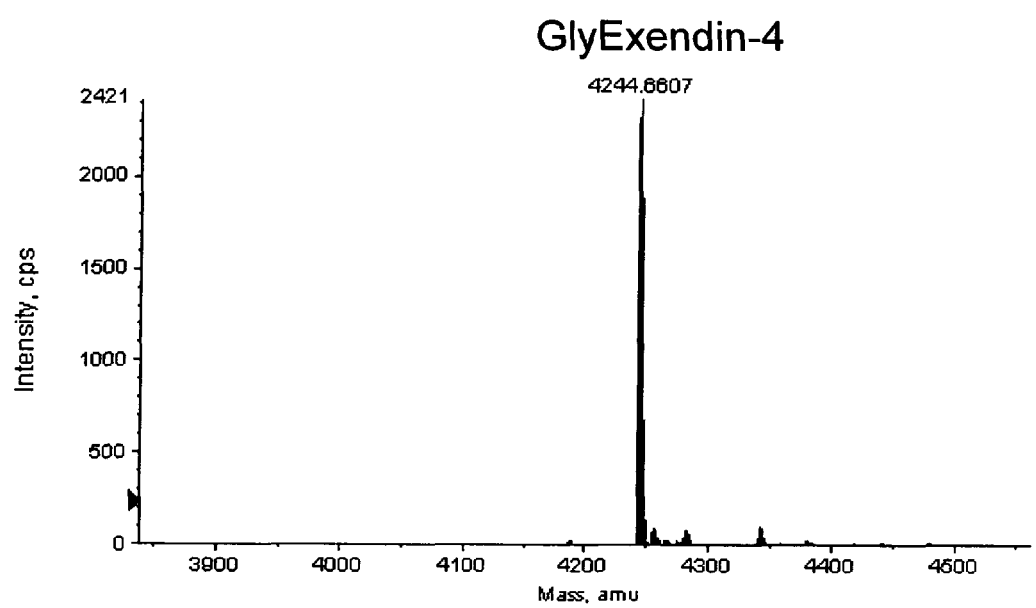

FIG. 7 HPLC chromatogram showing N-2 impurities from DAP2 disrupted *Pichia pastoris* host FIG. 8 ESI-TOF analysis of culture supernatant from *Pichia pastoris* with STE13 gene disruption, showing the mass of GlyExendin-4.

Figure 9:
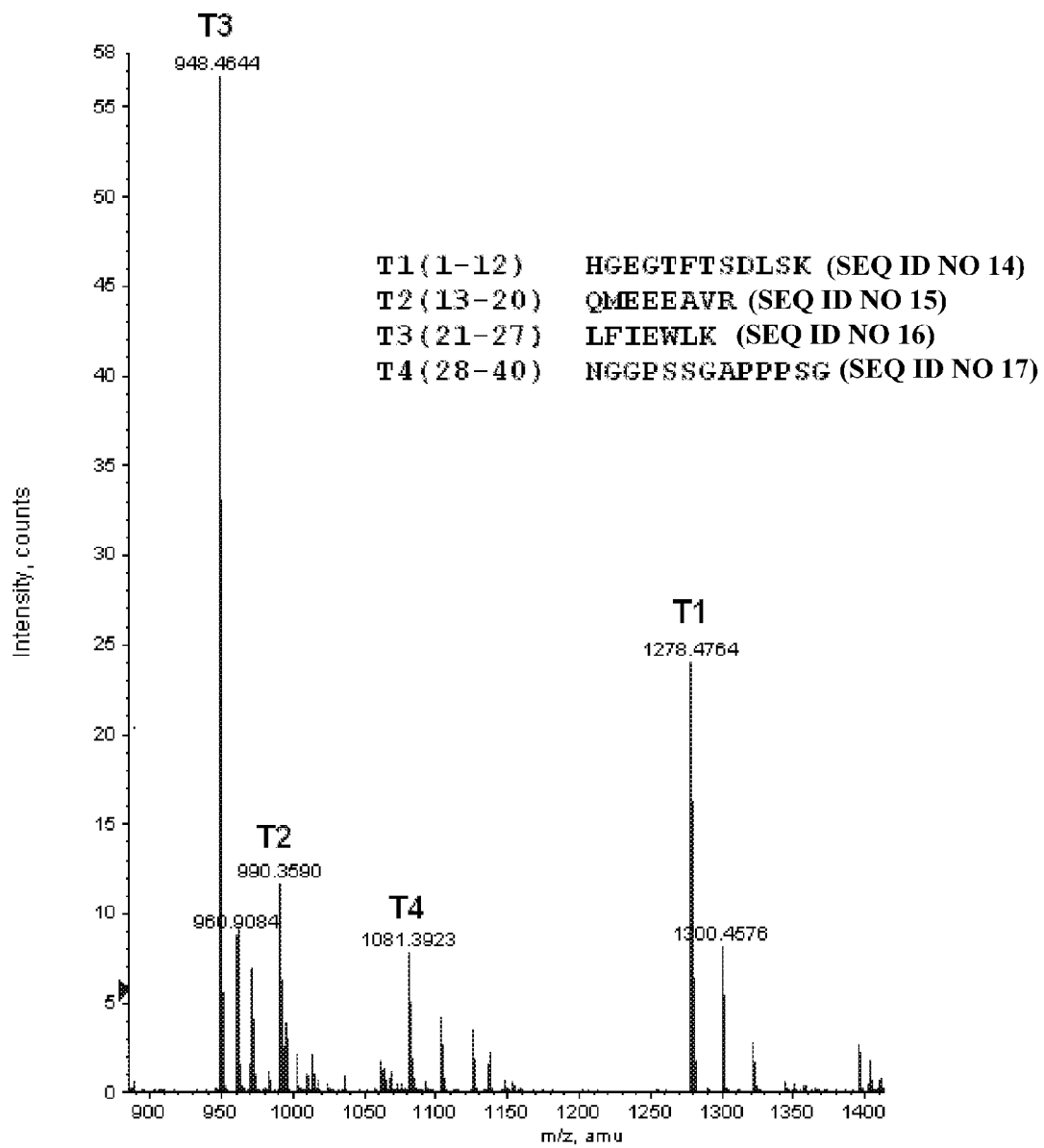

FIG. 9 Tryptic map of GlyExendin-4

The present invention provides a system for preparing insulinotropic peptides by efficient expression of heterologous gene in microorganisms. This system provides for large-scale recombinant production of peptide precursor such as GlyExendin-4. The system provides a way of producing large quantities of biologically active peptides without resorting to solid phase peptide synthesis. The peptides produced using the inventive system may be used in formulating pharmaceutical compositions. The peptides and compositions thereof may be used in treating diabetes mellitus, reducing gastric motility, delaying gastric emptying, preventing hyperglycemia, and reducing appetite and food intake.

In producing an insulinotropic peptide by heterologous gene expression in a microorganism, the encoding polynucleotide sequence for the peptide, preferably as part of a vector, is transformed into a microorganism. The expression of the gene encoding the insulinotropic peptide is controlled by a promoter (e.g., an inducible promoter or a constitutive promoter). Preferably, the promoter is a strong promoter, more preferably a strong inducible promoter, which allows for the production of large quantities of the insulinotropic peptide. The cells transformed with the gene may be fungal (e.g., yeast (e.g., *Saccharomyces cerevisiae, Pichia pastoris*)). For expression in *Pichia pastoris*, the promoter used to drive the expression of the gene is preferably the AUG1 promoter, the GAP promoter (a strong constitutive promoter), or the AOX1 or AOX2 promoter (a strong inducible promoter); and the vector may be derived from a known or commercially available vector such as pPIC, pPIC3K, pPIC9K, or pHIL-D. For expression in *S. cerevisiae*, the promoter used may be the CUPI promoter, ADH promoter, the TEF1 promoter, or the GAL promoter. The polynucleotide sequence encoding the insulinotropic peptide being expressed may be optimized for expression in the particular organism (e.g., codon usage may be optimized for use in the host microorganism). The polynucleotide sequence may optionally include leader sequences, signal sequences, pre-/pro-peptide sequences, tags for processing, tags for detection or purification, fusion peptides, etc. In certain embodiments, the gene encodes a signal peptide. The signal peptide may direct the processing or secretion of the peptide. In certain embodiments, the signal peptide is the signal peptide of Exendin-4 or the signal peptide of mat alpha factor. In certain embodiments, the gene encodes a propeptide, and the propeptide includes the native Exendin-4 propeptide or the propeptide of Mat alpha factor (see WO 98/35033; Pohl et al., *J. Biol. Chem.* 273:9778-9784, 1998; each of which is incorporated herein by reference).

The transformed host cells are selected for the presence of the vector (e.g., antibiotic resistance, ability to grow on media which does not contain a particular nutrient) and/or expression of the exogenous gene encoding the insulinotropic peptide. The selected cells are then grown under conditions suitable for expression of the gene encoding the peptide. In certain embodiments, the medium in which the cells are grown include an agent, such as methanol, which induces the expression of the gene encoding the peptide. In other embodiments, when a constitutive promoter is used, an agent for inducing the expression for the exogenous gene is not necessary. The transformed host cell produces the peptide. Preferably, peptide is properly processed by the host cell. That is, the peptide is properly folded and post-translationally modified. In certain embodiments, the peptide is secreted into the growth medium. The recombinantly produced peptide is then isolated and purified from the host cells or from the medium, if the peptide has been secreted. The purified peptide may be further modified chemically or enzymatically (e.g., alpha amidation, cleavage).

In one aspect, the insulinotropic peptide, GlyExendin-4, is produced. The GlyExendin-4 in *Pichia pastoris* involves preparing the expression construct comprising a signal sequence, a pro-peptide, a pre-peptide, and/or a tag, which is followed by the 40 amino acid GlyExendin-4 sequence in tandem. In certain embodiments, the signal sequence comprises the native Exendin-4 signal sequence of 23 amino acid or a 19 amino acid alpha factor signal sequence. The propeptide comprises the native GlyExendin-4 propeptide of 24 amino acids or a 66-amino acid propeptide of alpha factor. The tag may aid in the processing of the peptide (Kjeldsen et al. *Biotechnol. Appl. Biochem.* 29:79-86, 1999; incorporated herein by reference). In certain embodiments, the tag is a charged amino acid sequence such as the EAEA spacer described in Example 6. A *Pichia* codon optimized nucleotide sequence coding for GlyExendin-4 optionally with a signal peptide or propeptide is prepared. The synthetic nucleotide sequence is then cloned into an appropriate vector carrying a selectable marker gene, such as pPIC, pPIC3K, pPIC9K, or pHIL-D. The vector is transformed into *Pichia pastoris* cells, and transformed cells carrying the vector are selected. The selected clone is fermented on a large enough scale to produce the desired quantity of GlyExendin-4 peptide. The GlyExendin-4 peptide so produced into the broth need no further processing steps to make it a fully functional peptide unlike that produced in bacterial system (EP 978565 Ohsuye et al Suntory limited; incorporated herein by reference). The peptide is purified from the medium using protein purification techniques known in the art. The GlyExendin-4 peptide is preferably not glycosylated by the *Pichia* host cells. Lack of glycosylation is also an advantage because the GlyExendin-4 is fully functional and it leads to a simpler and easier purification process and results in improved yields of the peptide. The purified GlyExendin-4 peptide may be further chemically or enzymatically modified (e.g., C-terminal alpha amidation). The Exendin-4 peptide may be used in pharmaceutical compositions for administration to a subject (e.g., humans).

A problem was encountered during the production of the GlyExendin-4 polypeptide in *Pichia pastoris*. The secreted polypeptide was found to be a mixture of full length and an N-terminally clipped molecule, lacking the first two amino acids, HG. The yield of full length Exendin could be increased by knocking out the *Pichia pastoris* homolog of *Saccharomyces cerevisiae* STE13 gene, which encodes for a dipeptidyl peptidase. This study also indicated for the first time, a novel recognition site for STE13 *Pichia* homolog; it also cleaves after N-terminal dipeptide sequence "HG".

DEFINITIONS

"Peptide" or "protein": According to the present invention, a "peptide" or "protein" comprises a string of at least three amino acids linked together by peptide bonds. The terms "protein" and "peptide" may be used interchangeably. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification (e.g., alpha amidation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide.

"Transformation": The term "transformation" as used herein refers to introducing a vector comprising a nucleic acid sequence into a host cell. The vector may integrate itself or a portion of itself into the chromosome of the cells, or the vector may exist as a self-replicating extrachromosomal vector. Integration is considered in some embodiments to be advantageous since the nucleic acid is more likely to be stably maintained in the host cell. In other embodiments, an extrachromosomal vector is desired because each host cell can contain multiple copies of the vector.

The instant invention provides a system for recombinantly producing insulinotropic peptides and is particularly useful in preparing large quantities of biologically active peptide for use in pharmaceutical compositions or for research purposes. The invention provides methods of preparing the polynucleotide and recombinant cells for producing the peptide as well as methods of recombinantly producing the peptide itself. The invention also includes polynucleotide sequences, vectors and cells useful in practicing the inventive methods, and pharmaceutical compositions and methods of using the recombinantly produced peptides.

As described above, recombinantly expressing an insulinotropic peptide in a host microorganism involves preparing a polynucleotide with the peptide-encoding sequence, introducing this sequence into a vector, transforming cells of the microorganism with the vector, and selecting for cells with the vector. These selected cells are then grown under suitable conditions to produce the insulinotropic peptide, which is purified from the cells or from the medium in which the cells were growing. The purified peptide is then used in pharmaceutical compositions to treat such diseases as diabetes or obesity.

After the peptide has been harvested from the fermentation, the peptide is purified. The peptide may be purified from the cells, or if the peptide is secreted, the peptide may be purified from the media. If the peptide is purified from cells, the cells are lysed, and the peptide is purified from the cell lysate. The peptide may be purified using any methods known in the art including ammonium sulfate precipitation, column chromatography (e.g. ion exchange chromatography, size exclusion chromatography, affinity chromatography), FPLC, HPLC (e.g., reverse phase, normal phase), etc. The peptide is purified to the desired level of purity. In certain embodiments, the final peptide is greater than 90% pure, 95% pure, 98% pure, or 99% pure, preferably greater than 98% pure.

The purified peptide may be used as is, or the peptide may be further modified. In certain embodiments, the peptide is treated with a protease to cleave the peptide. In other embodiments, the peptide is phosphorylated. In yet other embodiments, the peptide is glycosylated. The peptide may be alpha-amidated. Other modifications may be performed on the peptide. The peptide may be modified chemically or enzymatically.

Production of GlyExendin-4 in *Pichia pastoris*

The production of recombinant GlyExendin-4 in *Pichia pastoris* involves preparing the expression construct comprising a signal sequence, an optional propeptide or a tag which is followed by the 40 amino acid GlyExendin-4 sequence in tandem. The signal sequence comprises the native Exendin-4 signal sequence of 23 amino acid or the 19 amino acid alpha factor signal sequence. The propeptide comprises native Exendin-4 propeptide of 24 amino acids or a 66 amino acid propeptide of alpha factor.

A synthetic, *Pichia* codon optimized GlyExendin-4 coding sequence (CDS) is engineered, and overlapping oligonucleotides of the sequence are prepared. The oligonucleotides are phosphorylated, annealed and ligated. PCR is performed to amplify the CDS, which is cloned into the restriction sites of an appropriate vector carrying a selectable marker gene. The vector is selected from pPIC, pPIC3K, pPIC9K, or pHIL-D. These vectors include the AOX promoter to drive the expression of the GlyExendin-4 gene. The vector carrying the synthetic GlyExendin-4 cDNA is transformed into *Pichia pastoris* cells, and the transformed cells are plated on minimal medium.

The transformed *Pichia* cells are plated on medium containing a selection agent to identify multicopy integrants and positive clones are selected. Fermentation with the positive clones are done, and the GlyExendin-4 peptide is purified from *Pichia* cell-free supernatant using a combination of chromatographic techniques which include ion exchange, hydrophobic, gel filtration, and/or affinity chromatography. In certain embodiments, the GlyExendin-4 peptide produced by the *Pichia* cells is a totally non-glycosylated product.

It was observed during expression of GlyExendin-4 that some products of its degradation occurred as impurities. These impurities were determined by Mass spec analysis to be forms of GlyExendin-4 clipped at the N-terminus by 2, 6 or 8 amino acids. The proportion of (N-2) GlyExendin-4 to full-length GlyExendin-4 was approximately 1:1. The other forms were found in much lower amounts and accumulated as the fermentation progressed. This problem was solved by disruption of the gene encoding *Saccharomyces cerevisiae* STE13 homolog in *Pichia*.

Purification and Modification of GlyExendin-4

The recombinant peptide or peptide conjugate having the polypeptide sequence of GlyExendin-4 is isolated and purified from the culture medium by separating the medium from the host cells, or if the peptide is produced in the cell, separating the cell debris after cell lysis. The peptide is then precipitated using salt or solvent and subjected to a variety of chromatographic procedures like ion exchange chromatography, hydrophobic interaction chromatography, affinity chromatography, and/or crystallization.

The GlyExendin-4 peptide has 40 amino acids. Optionally, the 39$^{th}$ amino acid, serine, is amidated. The 40 amino acid peptide is amidated in vitro to yield an GlyExendin-4 peptide of 39 amino acids with the C-terminal amino acid amidated, that is, the C-terminal glycine is removed and the penultimate serine is amidated. In certain embodiments, the amidation is accomplished using a C-terminal alpha-amidating enzyme.

The biological activity of GlyExendin-4 and the 39 amino acid amidated version is determined by its ability to induce the secretion of insulin in a rat insulinoma cell line.

The technology of the instant application is further elaborated with the help of following examples. However, these examples should not be construed to limit the scope of the invention.

EXAMPLE 1

Synthesis of Codon Optimized GlyExendin-4 CDS

A codon optimized nucleotide sequence coding for GlyExendin-4 (Sequence ID No: 5) was synthesized by polymerase chain reaction (PCR) using overlapping oligonucleotides. Ten oligonucleotides were synthesized to cover the GlyExendin-4 gene along both strands having 14 bp overlapping region with the successive primers. The overlapping oligonucleotides were phosphorylated in a reaction mixture containing 10×PNK buffer, T4 polynucleotide kinase, and dATP. Equimolar amounts of phosphorylated oligonucleotides were annealed and then ligated using T4 DNA ligase.

The ligation mixture was used as a template for amplification of the GlyExendin-4 CDS by PCR using the oligonucleotides, 5'-CTC GAG AAA AGA CAT GGA GAA GGA ACA TTT ACA TC-3' (Sequence ID No: 6) (forward primer) and 5'-GAA TTC TTA TCC AGA TGG TGG-3' (Sequence ID No: 7) (reverse primer). The PCR reaction was performed according to standard protocols, and amplification was done in a final volume of 50 µL using Pfu Turbo polymerase (Stratagene). The amplification conditions included an initial denaturation of 4 minutes at 94° C. for one cycle, followed by 30 cycles (denaturation at 94° C. for 30 seconds; annealing at 60° C. for 30 seconds; extension at 72° C. for 60 seconds) and a final extension for 10 minutes for one cycle in a Perkin-Elmer Thermal cycler.

EXAMPLE 2

Cloning of Codon Optimized GlyExendin-4 CDS into Sequencing Vector

The 140 bp PCR fragment obtained after amplification was cloned into the vector pTZ57RT/A using a TA cloning kit (Fermentas), in a reaction mix containing 3 µl of vector, 2 µl PEG4000 PCR buffer, and 1 µl T4 DNA ligase. DH5α competent cells were transformed, and positive clones containing the GlyExendin-4 gene fragment were screened by restriction digestion. One of the positive clones was sequenced on both strands.

EXAMPLE 3

Subcloning of GlyExendin-4 CDS into an Expression Vector

The GlyExendin-4 fragment from the TA clone (see Example 2) was excised using EcoRI and XhoI and sub cloned into the same sites of the *Pichia pastoris* expression vector pPIC9K (Invitrogen, San Diego, Calif.). This placed GlyExendin-4 nucleotide sequence in frame with the *Saccharomyces cerevisiae* Mat alpha signal peptide and under the control of the methanol-inducible alcohol oxidase (AOXI) promoter (FIG. 1). The expression vector was transformed into *Pichia pastoris* by electroporation as described in the invitrogen manual.

EXAMPLE 4

Expression of GlyExendin-4 in *Pichia pastoris* Host

Transformation

The expression plasmid having the *Pichia* codon optimized nucleotide insert was introduced into *Pichia pastoris*, GS115 strain (his4, Mut$^+$) by electroporation as described in the Invitrogen manual. The conditions used for electroporation were charging voltage of 1.5 kV, capacitance of 25 µF, and resistance of 200Ω. The transformed cells were plated on minimal medium (YNBD) lacking histidine and incubated at 30° C. for 3 days.

Screening for Multicopy Integrants

Single colonies of transformants were picked and grown in microtitre plates containing YPD (1% yeast extract, 2% Bacto-Peptone, 2% dextrose) at 30° C. overnight. The pregrown cultures were replica-plated onto YPD agar plates with Geneticin (2 mg/ml) and incubated at 30° C. Clones growing on YPD-Geneticin (2 mg/ml) plate were selected for carrying out expression studies.

Small Scale Induction of GlyExendin-4

GlyExendin-4 expression was induced using the following protocol:

Inoculate culture grown in agar plates (YEPD) into YNBG (Yeast Nitrogen Base Glycerol) medium-50 ml in 250 ml flask YNBG Composition (for 100 ml)

Yeast Nitrogen Base (YNB) without amino acids: 1.34 g in 90 ml

Glycerol: 20% 10 ml

Grow overnight in YNBG medium. Transfer to BYYG (50 ml in 250 ml) such that the starting OD is 0.3.

BYYG Composition (for 100 ml)

Bactopeptone: 1 g

Yeast extract: 2 g

YNB without aa: 1.34 g

Glycerol: 20% 10 ml

1M $KH_2PO_4$, pH 6: 10 ml

Grow for 2 days. Spin, weigh the pellet and resuspend in induction media (BYYM). 3 g pellet in 6 ml media and transfer to 100 ml flask.

Induction Media Composition (for 100 ml)

Bactopeptone: 1 g

Yeast extract: 2 g

YNB without aa: 1.34 g

Methanol: 3 ml

1M $KH_2PO_4$, pH 6: 10 ml

Feed methanol and Nitrogen everyday (for 2 consecutive days) and harvest on third day.

Nitrogen: 120 µl of 5×YP (0.1×YP)

Methanol: 180 µl of 100% methanol (3%)

5×YP Composition (for 50 ml)

Yeast Extract: 2.5 g

Bactopeptone: 5 g

The induced cells were pelleted by centrifugation and the cell-free supernatant was analysed for GlyExendin-4 by tricine gel electrophoresis and HPLC. Although a single band of the expected size was observed on the gel, two peaks of GlyExendin-4 could be resolved with HPLC (FIG. 2). These two peaks were analysed by mass analysis and were found to correspond to the full-length and N-terminally clipped (N-terminal aminoacids HG absent; (N-2)) forms of GlyExendin-4.

EXAMPLE 5

Cloning of GlyExendin-4 in *Pichia pastoris* Using a Spacer Sequence

The codon optimized nucleotide sequence coding for GlyExendin-4 is cloned in tandem with and a spacer sequence coding for EAEA at its N-terminal end into a *Pichia pastoris* vector pPIC9K. The expression vector carrying the insert was transformed into *Pichia pastoris*. Upon expression of the polypeptide the Mat-α which ends with Lys-Arg is cleaved from the peptide by the action of KEX2 protease while the spacer peptide is cleaved by a STE13 protease allowing the release of GlyExendin-4. Analysis of GlyExendin-4 expressed using this construct did not help in eliminating or reducing the proportion of (N-2) GlyExendin-4.

EXAMPLE 6

Disruption of *Pichia* Homolog of *Saccharomyces cerevisiae* STE13 Gene in GlyExendin-4 Producing *Pichia pastoris* Clone The removal of two aminoacids from the N-terminus of GlyExendin-4 suggested the activity of a dipeptidylpeptidase. *Pichia* homologs of two dipeptidyl peptidases DAP2 and STE13 were carried out in an attempt to eliminate the (N-2) impurity.

The dipeptidyl peptidase gene homolog (STE13) of *Saccharomyces cerevisiae*, was disrupted in *Pichia pastoris* by insertional inactivation. Putative *Pichia pastoris* homolog of STE13 gene (which encodes a trans-golgi dipeptidyl peptidase) of *Saccharomyces cerevisiae* was identified using BLASTP. The *Pichia* STE13 nucleotide sequence was provided by Prof. James Cregg. A ~450 bp region expected to disrupt the catalytic domain of the enzyme was chosen and amplified by PCR from the genomic DNA of the *Pichia pastoris* strain GS115. The fragment was then cloned into a suitable vector, linearised within the region of homology and transformed into the GlyExendin-4 producing *Pichia* strain to achieve disruption. Selection was done on YEPD/1M Sorbitol plates containing 100 µg/ml Zeocin. About 900 of these transformants were inoculated into YEPD in 96-well plates. After overnight growth these were replica-plated on YEPD plates and screened for the absence of STE13 by means of a plate assay. Putative disruptants identified by the assay were screened by PCR to check if the locus was disrupted. The clone that was confirmed to have STE13 locus disrupted was taken up for further analysis.

Construction of STE13 Disruption Vector

The coding sequence of STE13 CDS and the fragment chosen to provide homology for targeting have been given in Sequence ID No: 8. The STE13 fragment was assembled in two PCR steps (FIG. 3). The first PCR step was done with Taq polymerase (Bangalore Genei, India) using the following primer pairs: IISTEFP1/IISTERP1 (PCR1; Sequence ID Nos: 9,10) and IISTEFP2/IISTERP2 (PCR2; Sequence ID Nos: 11,12). PCR cycling parameters: Initial denaturation at 94° C. for 4 min followed by 30 cycles of denaturation at 94° C. for 30 s, annealing at 60° C. for 30 s and extension at 72° C. for 30 s; Final extension was done at 72° C. for 10 min. The genomic DNA of GS115 was used as the template for this PCR. The primers incorporated a restriction site (NdeI) at approximately the centre of the fragment. This provided a restriction site to linearise the construct within the homologous region. The second PCR step was an overlap PCR done using XT Taq polymerase (Bangalore Genei, India), with the two amplified fragments as template to generate the 450 bp fragment. Primers used for overlap PCR: IISTEFP1/IISTERP2. PCR cycling parameters: Same as PCR1, but modified to include 3 cycles of denaturation at 94° C. for 45 s, annealing at 37° C. for 45 s and extension at 72° C. for 30 s, after the initial denaturation step to facilitate overlap. Restriction sites were also introduced at the 5' and 3' ends of the fragments to facilitate cloning. The 450 bp fragment was first cloned into pTZ57R-TA vector (Fermentas, Canada) and its identity was confirmed by sequencing. It was then subcloned into pPICZA (Invitrogen, USA) at the BamHI/BglII sites to get Stefrg/pPICZA (FIG. 4). After linearization of Stefrg/pPICZA by NdeI, the construct was transformed into the *Pichia pastoris* strain producing GlyExendin-4 by electroporation (Method described earlier in Example 4).

Plate Assay

The assay has been described previously for *Saccharomyces cerevisiae* (Rendueles and Wolf, (1987) J. Bacteriol., 169 (9): 4041-4048). Briefly, the colonies were first lysed by flooding the plates with chloroform. After the chloroform evaporated completely, a mixture of the substrate, Ala-Pro-4MβNA and Fast garnet GBC in 1% Tris agar was poured to form an overlay. This was incubated at room temperature for about 10-15 minutes. Colonies that did not stain red were picked up as STE13 disruptants. GS115 with intact STE13 was included as a control to check the progress of staining.

PCR Analysis

Genomic DNA was isolated from those transformants that were picked up as positives in the plate assay and the disruption of STE13 locus was confirmed by PCR. A forward primer upstream of the region of homology and a reverse primer from the vector sequence were designed such that an amplication of ~800 bp will be observed in the disruptant. The undisrupted locus should not show any amplification. Of the positives obtained by PCR analysis (FIG. 5), the clone D2 was taken up for further analysis.

Clone D2 was induced with methanol (Method as described in Example 4) and the expressed GlyExendin-4 when checked by HPLC and LCMS was not N-terminally clipped. This clearly shows that STE13 dipeptidyl peptidase activity was responsible for the N-terminal clipping of GlyExendin-4 (FIG. 6).

Disruption of the *Pichia* homolog of the *Saccharomyces cerevisiae* dipeptidyl peptidase gene DAP2 was carried out in the *Pichia* clone expressing GlyExendin-4 in a similar manner (data not shown). This continued to show (N-2) impurity indicating that it was not responsible for generation of this impurity (see FIG. 7).

EXAMPLE 7

Fermentation of *Pichia pastoris* for Expression of GlyExendin-4

*Pichia* cells freshly thawed from a vial stored at −70° C. were inoculated into 50 ml growth medium (1% yeast extract, 2% peptone, 10% 1M phosphate buffer of pH 6.0, 0.67% yeast nitrogen base, and 0.1% glycerol) and cultivated at 28-32° C. and 220-260 rpm. The seed cells are cultivated in 2 L fermentor containing one liter of fermentation medium consisting of 4% glycerol, 0.01% calcium sulfate, 2% potassium sulfate, 1.4% magnesium sulfate, and 0.4% potassium hydroxide. Fermentor experiments with the above medium were performed at different temperatures ranging from 20° C. to 30° C., pH 5.0, aeration rate 0.5-2.0 vvm. Agitation speed was increased gradually from 350 to 1200 rpm to maintain the dissolved oxygen level above 30%. Biomass was built up to 300 g/L by 50% glycerol feeding. Aseptically 1 L broth was harvested and 50 ml of broth was dispensed in each of twelve 250 ml flasks. All flasks were incubated at different temperatures ranging from 20° C. to 30° C. at 220 to 260 rpm. 100 μL of methanol was added every day, and after five days analysis for GlyExendin-4 expression was performed.

Samples were taken every 24 hours after methanol feeding, and GlyExendin-4 levels were determined using HPLC. GlyExendin-4 yields obtained after 5 days of fermentation at different growth temperatures is given below.

TABLE 1

| Growth temperature (° C.) | Yield of GlyExendin-4 (g/L) |
|---|---|
| 20 | 0.0443 |
| 22 | 0.0467 |
| 24 | 0.0567 |
| 26 | 0.0867 |
| 28 | 0.0905 |
| 30 | 0.0685 |

EXAMPLE 8

Fermentation of Recombinant *Pichia* for Production of GlyExendin-4

*Pichia* cells freshly thawed from a vial stored at −70° C. were inoculated into 50 ml growth medium (1% yeast extract, 2% peptone, 10% 1M phosphate buffer (pH 6.0), 0.67% yeast nitrogen base, and 0.1% glycerol) at 28-32° C. and 220-260 rpm. The seed cells are cultivated in a 2 L fermentor containing one liter of fermentation medium (3.5% glycerol, 0.01% calcium sulfate, 1% potassium sulfate, 1% magnesium sulfate, 0.25% potassium hydroxide). Fermentor experiments with the above medium were performed at different temperatures ranging from 20° C. to 30° C., pH 5.0, aeration rate 0.5-2.0 vvm. Agitation speed was increased gradually from 350 to 1200 rpm to maintain the dissolved oxygen level above 30%. Biomass was built up to 285 g/L by 50% glycerol feeding, and then methanol feeding was carried out.

Samples were taken every 24 hour after methanol feeding, and GlyExendin-4 levels were determined using HPLC. GlyExendin-4 yields obtained after 5 days of fermentation at different growth temperatures is given below.

TABLE 2

| Growth temperature (° C.) | Yield of GlyExendin-4 (g/L) |
|---|---|
| 20 | 0.23 |
| 22 | 0.37 |
| 24 | 0.67 |
| 26 | 0.72 |
| 28 | 0.75 |
| 30 | 0.67 |

EXAMPLE 9

Characterisation of GlyExendin-4 Expressed in *Pichia*

GlyExendin-4 was purified from the cell-free supernatant after fermentation using standard chromatographic techniques. The purified peptide had a mass of 4.2 kDa as characterized by ESI-TOF (FIG. 8) which corresponds to full-length GlyExendin-4, strongly indicating the absence of N-terminal clipping and glycosylated species. N-terminal sequencing (Sequence ID No: 13) further confirmed the absence of N-terminal degradation. The sequence of the expressed peptide was confirmed by tryptic digest (FIG. 9) followed by sequencing of the individual fragments (Sequence ID Nos: 14-17). This confirmed further the absence of glycosylated species.

OTHER EMBODIMENTS

The foregoing has been a description of certain non-limiting preferred embodiments of the invention. Those of ordi-

We claim:

1. A method of producing a biologically active Exendin-4 having an N-terminal recognition site His-Gly, said Exendin-4 having insulinotropic activity, the method comprising steps of:
   a) transforming a genetically modified *Pichia pastoris* with a polynucleotide vector encoding Glyexendin-4, wherein protease gene STE13 of the *Pichia pastoris* has been knocked-out;
   b) growing the transformed *Pichia pastoris* to produce the Glyexendin-4; and
   c) isolating and alpha-amidating the Glyexendin-4 to produce the biologically active Exendin-4.

2. The method as claimed in claim 1, wherein the glyexendin-4 is contacted with a C-terminal alpha-amidating enzyme to yield the alpha-amidated biologically active Exendin 4.

3. The method as claimed in claim 2, wherein the alpha-amidated Exendin-4 polypeptide is set forth as SEQ ID NO. 2 (HGEGTFTSDLSKQMEEEAVR-LFIEWLKNGGPSSGAPPPS-NH2).

4. The method as claimed in claim 1, wherein the Glyexendin-4 has the polypeptide sequence set forth as SEQ ID NO 4.

5. The method as claimed in claim 1, wherein the gene encoding Glyexendin-4 has the polynucleotide sequence set forth as SEQ ID NO 5.

6. The method as claimed in claim 1, wherein the transformed cells are grown under conditions that induce expression of the polypeptide.

7. A method of producing Glyexendin-4 having an N-terminal recognition site His-Gly, said Glyexendin-4 having an insulinotropic activity, the method comprising steps of:
   a. transforming a genetically modified *Pichia pastoris* with a polynucleotide vector encoding the Glyexendin-4, wherein protease gene STE13 of the *Pichia pastoris* has been knocked out; and
   b. growing the transformed Pichia pastoris to produce the Glyexendin-4.

8. The methods as claimed in claim 7, wherein the Glyexendin-4 has the polypeptide sequence set forth as SEQ ID NO 4.

9. The method as claimed in claim 8, wherein the Glyexendin-4 is encoded by the polynucleotide sequence set forth as SEQ ID NO 5.

10. The method as claimed in claim 7, further comprising contacting the glyexendin-4 polypeptide with a C-terminal alpha-amidating enzyme to yield an alpha-amidated exendin-4 polypeptide.

11. The method as claimed in claim 10, wherein the alpha-amidated Exendin-4 polypeptide has the sequence set forth as SEQ ID NO. 2 (HGEGTFTSDLSKQMEEEAVR-LFIEWLKNGGPSSGAPPPS-NH2).

12. The method as claimed in claim 7, wherein the protease gene STE13 is an N-terminal dipeptidyl peptidase gene.

13. The method as claimed in claim 7, wherein the transformed cells are grown under conditions that induce expression of the Glyexendin-4.

14. The method as claimed in claim 1, wherein the protease gene STE13 is an N-terminal dipeptidyl peptidase gene.

* * * * *

SEQUENCE LISTING

<160> NUMBER OF SEQ ID NOS: 18

<210> SEQ ID NO 1
<211> LENGTH: 87
<212> TYPE: PRT
<213> ORGANISM: Heloderma suspectum
<220> FEATURE:
<221> NAME/KEY: PEPTIDE
<222> LOCATION: (1)..(87)
<223> OTHER INFORMATION: Amino acid sequence of Exendin-4 precursor

<400> SEQUENCE: 1

Met Lys Ile Ile Leu Trp Leu Cys Val Phe Gly Leu Phe Leu Ala Thr
1               5                   10                  15

Leu Phe Pro Ile Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Gly Glu Gly Thr Phe Thr Ser Asp Leu Ser Lys Gln Met Glu Glu
    50                  55                  60

Ala Val Arg Leu Phe Ile Glu Trp Leu Lys Asn Gly Gly Pro Ser Ser
65                  70                  75                  80

Gly Ala Pro Pro Ser Gly
                85

<210> SEQ ID NO 2
<211> LENGTH: 39
<212> TYPE: PRT
<213> ORGANISM: Heloderma suspectum
<220> FEATURE:
<221> NAME/KEY: PEPTIDE
<222> LOCATION: (1)..(39)
<223> OTHER INFORMATION: Amino acid sequence of Exendin-4

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 3
<211> LENGTH: 31
<212> TYPE: PRT
<213> ORGANISM: Homo sapiens
<220> FEATURE:
<221> NAME/KEY: MISC_FEATURE
<222> LOCATION: (1)..(31)
<223> OTHER INFORMATION: Amino acid sequence of active GLP-1 (7-37)

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 40
<212> TYPE: PRT

```
<213> ORGANISM: Heloderma suspectum
<220> FEATURE:
<221> NAME/KEY: MISC_FEATURE
<222> LOCATION: (1)..(40)
<223> OTHER INFORMATION: Amino acid sequence of GlyExendin-4

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly
        35                  40

<210> SEQ ID NO 5
<211> LENGTH: 141
<212> TYPE: DNA
<213> ORGANISM: Artificial Sequence
<220> FEATURE:
<223> OTHER INFORMATION: Nucleotide sequence encoding Exendin-4,
      optimized for expression in Pichia pastoris
<220> FEATURE:
<221> NAME/KEY: misc_feature
<222> LOCATION: (1)..(141)
<223> OTHER INFORMATION: Nucleotide sequence encoding Extendin-4,
      optimized for expression in Pichia pastoris

<400> SEQUENCE: 5
ctcgagaaaa gacatggaga aggaacattt acatctgatt tgtctaaaca aatggaagaa      60
gaagctgtta gattgtttat tgaatggttg aaaaacggag gaccatcttc tggagctcca     120
ccaccatctg gataagaatt c                                               141

<210> SEQ ID NO 6
<211> LENGTH: 35
<212> TYPE: DNA
<213> ORGANISM: Artificial Sequence
<220> FEATURE:
<223> OTHER INFORMATION: PCR primer (forward) for amplification of
      Exendin-4 CDS
<220> FEATURE:
<221> NAME/KEY: misc_feature
<222> LOCATION: (1)..(35)
<223> OTHER INFORMATION: PCR primer (forward) for amplification of
      Exendin-4 CDS

<400> SEQUENCE: 6
ctcgagaaaa gacatggaga aggaacattt acatc                                35

<210> SEQ ID NO 7
<211> LENGTH: 21
<212> TYPE: DNA
<213> ORGANISM: Artificial Sequence
<220> FEATURE:
<223> OTHER INFORMATION: PCR primer (reverse) for amplification of
      Exendin-4 CDS
<220> FEATURE:
<221> NAME/KEY: misc_feature
<222> LOCATION: (1)..(21)
<223> OTHER INFORMATION: PCR primer (reverse) for amplification of
      Exendin-4 CDS

<400> SEQUENCE: 7
gaattcttat ccagatggtg g                                               21

<210> SEQ ID NO 8
<211> LENGTH: 2553
<212> TYPE: DNA
<213> ORGANISM: Pichia pastoris
```

<220> FEATURE:
<221> NAME/KEY: misc_feature
<222> LOCATION: (1)..(2553)
<223> OTHER INFORMATION: Nucleotide sequence of STE13 CDS

<400> SEQUENCE: 8

| | | | | | |
|---|---|---|---|---|---|
| atgacatctc | ggacagctga | gaacccgttc | gatatagagc | ttcaagagaa | tctaagtcca | 60 |
| cgttcttcca | attcgtccat | attggaaaac | attaatgagt | atgctagaag | acatcgcaat | 120 |
| gattcgcttt | cccaagaatg | tgataatgaa | gatgagaacg | aaaatctcaa | ttatactgat | 180 |
| aacttggcca | agttttcaaa | gtctggagta | tcaagaaaga | gctgtatgct | aatatttggt | 240 |
| atttgctttg | ttatctggct | gtttctcttt | gccttgtatg | cgagggacaa | tcgatttttcc | 300 |
| aatttgaacg | agtacgttcc | agattcaaac | agccacggaa | ctgcttctgc | caccacgtct | 360 |
| atcgttgaac | caaaacagac | tgaattacct | gaaagcaaag | attctaacac | tgattatcaa | 420 |
| aaaggagcta | aattgagcct | tagcggctgg | agatcaggtc | tgtacaatgt | ctatccaaaa | 480 |
| ctgatctctc | gtggtgaaga | tgacatatac | tatgaacaca | gttttcatcg | tatagatgaa | 540 |
| aagaggatta | cagactctca | acacggtcga | actgtattta | actatgagaa | aattgaagta | 600 |
| aatgcaatca | cgtatacagt | gtcatttgtc | accatttctc | cttacgattc | tgccaaattc | 660 |
| ttagtcgcat | gcgactatga | aaaacactgg | agacattcta | cgtttgcaaa | atatttcata | 720 |
| tatgataagg | aaagcgacca | agaggatagc | tttgtacctg | tctacgatga | caaggcattg | 780 |
| agcttcgttg | aatggtcgcc | ctcaggtgat | catgtagtat | tcgtttttga | aaacaatgta | 840 |
| tacctcaaac | aactctcaac | tttagaggtt | aagcaggtaa | cttttgatgg | tgatgagagt | 900 |
| atttacaatg | gtaagcctga | ctggatctat | gaagaggaag | ttttaagtag | cgacagagcc | 960 |
| atatggtgga | tgacgatgg | atcgtacttt | acgttcttga | gacttgatga | cagcaatgtc | 1020 |
| ccaaccttca | acttgcagca | ttttttttgaa | gaaacaggct | ctgtgtcgaa | atatccggtc | 1080 |
| attgatcgat | tgaaatatcc | aaaaccagga | tttgacaacc | ccctggtttc | tttgtttagt | 1140 |
| tacaacgttg | ccaagcaaaa | gttagaaaag | ctaaatattg | gagcagcagt | ttctttggga | 1200 |
| gaagacttcg | tgcttacag | tttaaaatgg | atagacaatt | cttttttctt | gtcgaagttc | 1260 |
| acagaccgca | cttcgaaaaa | aatggaagtt | actctagtgg | acattgaagc | caattctgct | 1320 |
| tcggtggtga | gaaaacatga | tgcaactgag | tataacggct | ggttcactgg | agaattttct | 1380 |
| gtttatcctg | tcgttggaga | taccattggt | tacattgatg | taatctatta | tgaggactac | 1440 |
| gatcacttgg | cttattatcc | agactgcaca | tccgataagt | atattgtgct | tacagatggt | 1500 |
| tcatggaatg | ttgttggacc | tggagtttta | gaagtgcttg | aagatagagt | ctactttatc | 1560 |
| ggcaccaaag | aatcatcaat | ggaacatcac | ttgtattata | catcattaac | gggacccaag | 1620 |
| gttaaggctg | ttatggatat | caagaaacct | gggtactttg | atgtaaacat | taagggaaaa | 1680 |
| tatgctttac | tatcttacag | aggccccaaa | ctcccatacc | agaaatttat | tgatctttct | 1740 |
| gaccctagta | caacaagtct | tgatgacatt | ttatcgtcta | atagaggaat | tgtcgaggac | 1800 |
| ggcgtcacac | tgaacatgat | tgaagtgttg | cctgccaatt | ttaatcctag | caagaagtac | 1860 |
| ccactgttgg | tcaacattta | tggtggaccg | ggctcccaga | agttagatgt | gcagttcaac | 1920 |
| attgggtttg | agcatattat | ttcttcgtca | ctggatgcaa | tagtgcttta | catagatccg | 1980 |
| agaggtactg | gaggtaaaag | ctgggctttt | aaatcttacg | ctacagagaa | aataggctac | 2040 |
| tgggaaccac | gagacatcac | tgcagtagtt | tccaagtgga | tttcagatca | ctcatttgtg | 2100 |
| aatcctgaca | aaactgcgat | atgggggtgg | tcttacggtg | ggttcactac | gcttaagaca | 2160 |
| ttggaatatg | attctggaga | ggttttcaaa | tatggtatgg | ctgttgctcc | agtaactaat | 2220 |

```
tggcttttgt atgactccat ctacactgaa agatacatga accttccaaa ggacaatgtt    2280
gaaggctaca gtgaacacag cgtcattaag aaggtttcca attttaagaa tgtaaaccga    2340
ttcttggttt gtcacgggac tactgatgat aacgtgcatt ttcagaacac actaaccttat   2400 ctggaccagt tcaatattaa tggtgttgtg aattacgatc ttcaggtgta tcccgacagt    2460
gaacatagca ttgcccatca caacgcaaat aaagtgatct acgagaggtt attcaagtgg    2520
ttagagcggg catttaacga tagatttttg taa                                 2553
```

```
<210> SEQ ID NO 9
<211> LENGTH: 30
<212> TYPE: DNA
<213> ORGANISM: Artificial Sequence
<220> FEATURE:
<223> OTHER INFORMATION: Primer (forward) for amplification of STE13
      targeting sequence from Pichia - PCR1
<220> FEATURE:
<221> NAME/KEY: misc_feature
<222> LOCATION: (1)..(30)
<223> OTHER INFORMATION: Primer (forward) for amplification of STE13
      targeting sequence from Pichia - PCR1

<400> SEQUENCE: 9
ggatccgcag ttcaacattg ggtttgagca                                     30

<210> SEQ ID NO 10
<211> LENGTH: 28
<212> TYPE: DNA
<213> ORGANISM: Artificial Sequence
<220> FEATURE:
<223> OTHER INFORMATION: Primer (reverse) for amplification of STE13
      targeting sequence
      from Pichia - PCR1
<220> FEATURE:
<221> NAME/KEY: misc_feature
<222> LOCATION: (1)..(28)
<223> OTHER INFORMATION: Primer (reverse) for amplification of STE13
      targeting sequence from Pichia - PCR1

<400> SEQUENCE: 10
ccagaatcat atgccaatgt cttaagcg                                       28

<210> SEQ ID NO 11
<211> LENGTH: 28
<212> TYPE: DNA
<213> ORGANISM: Artificial Sequence
<220> FEATURE:
<223> OTHER INFORMATION: Primer (forward) for amplification of STE13
      targeting sequence from Pichia - PCR2
<220> FEATURE:
<221> NAME/KEY: misc_feature
<222> LOCATION: (1)..(28)
<223> OTHER INFORMATION: Primer (forward) for amplification of STE13
      targeting sequence from Pichia - PCR2

<400> SEQUENCE: 11
cgcttaagac attggcatat gattctgg                                       28

<210> SEQ ID NO 12
<211> LENGTH: 30
<212> TYPE: DNA
<213> ORGANISM: Artificial Sequence
<220> FEATURE:
<223> OTHER INFORMATION: Primer (reverse) for amplification of STE13
      targeting sequence from Pichia - PCR2
<220> FEATURE:
<221> NAME/KEY: misc_feature
<222> LOCATION: (1)..(30)
<223> OTHER INFORMATION: Primer (reverse) for amplification of STE13
```

-continued targeting sequence from Pichia - PCR2

<400> SEQUENCE: 12
agatctgtcc cgtgacaaac caagaatcgg                                              30

<210> SEQ ID NO 13
<211> LENGTH: 10
<212> TYPE: PRT
<213> ORGANISM: Heloderma suspectum
<220> FEATURE:
<221> NAME/KEY: PEPTIDE
<222> LOCATION: (1)..(10)
<223> OTHER INFORMATION: N-Terminal of GlyExtendin-4; Results of
      N-terminal sequencing

<400> SEQUENCE: 13

His Gly Glu Gly Thr Phe Thr Ser Asp Leu
1               5                   10

<210> SEQ ID NO 14
<211> LENGTH: 12
<212> TYPE: PRT
<213> ORGANISM: Heloderma suspectum
<220> FEATURE:
<221> NAME/KEY: PEPTIDE
<222> LOCATION: (1)..(12)
<223> OTHER INFORMATION: Fragment obtained on tryptic digest of
      GlyExendin-4 - corresponds to peak T1 in Figure 9

<400> SEQUENCE: 14

His Gly Glu Gly Thr Phe Thr Ser Asp Leu Ser Lys
1               5                   10

<210> SEQ ID NO 15
<211> LENGTH: 8
<212> TYPE: PRT
<213> ORGANISM: Heloderma suspectum
<220> FEATURE:
<221> NAME/KEY: PEPTIDE
<222> LOCATION: (1)..(8)
<223> OTHER INFORMATION: Fragment obtained on tryptic digest of
      GlyExendin-4 - corresponds to peak T2 in Figure 9

<400> SEQUENCE: 15

Gln Met Glu Glu Glu Ala Val Arg
1               5

<210> SEQ ID NO 16
<211> LENGTH: 7
<212> TYPE: PRT
<213> ORGANISM: Heloderma suspectum
<220> FEATURE:
<221> NAME/KEY: PEPTIDE
<222> LOCATION: (1)..(7)
<223> OTHER INFORMATION: Fragment obtained on tryptic digest of
      GlyExendin-4 - corresponds to peak T3 in Figure 9

<400> SEQUENCE: 16

Leu Phe Ile Glu Trp Leu Lys
1               5

<210> SEQ ID NO 17
<211> LENGTH: 13
<212> TYPE: PRT
<213> ORGANISM: Heloderma suspectum
<220> FEATURE:
<221> NAME/KEY: PEPTIDE
<222> LOCATION: (1)..(13)
<223> OTHER INFORMATION: Fragment obtained on tryptic digest of
      GlyExendin-4 - corresponds to peak T4 in Figure 9

```
<400> SEQUENCE: 17

Asn Gly Gly Pro Ser Ser Gly Ala Pro Pro Pro Ser Gly
1               5                   10

<210> SEQ ID NO 18
<211> LENGTH: 39
<212> TYPE: PRT
<213> ORGANISM: Heloderma suspectum
<220> FEATURE:
<221> NAME/KEY: PEPTIDE
<222> LOCATION: (1)..(39)
<223> OTHER INFORMATION: C-terminal alpha-Serine amidated exendin-4

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```